United States Patent [19]
Quinn et al.

[11] Patent Number: 5,720,293
[45] Date of Patent: Feb. 24, 1998

[54] DIAGNOSTIC CATHETER WITH MEMORY

[75] Inventors: Michael D. Quinn; Mark L. Yelderman, both of Plano, Tex.

[73] Assignee: Baxter International Inc., Deerfield, Ill.

[21] Appl. No.: 245,727

[22] Filed: May 18, 1994

Related U.S. Application Data

[63] Continuation-in-part of Ser. No. 769,536, Oct. 1, 1991, abandoned, which is a continuation-in-part of Ser. No. 647,578, Jan. 29, 1991, abandoned, and a continuation-in-part of Ser. No. 49,231, Apr. 19, 1993, which is a continuation-in-part of Ser. No. 647,578, Jan. 29, 1991, abandoned.

[51] Int. Cl.$^6$ ...................................................... A61B 5/02
[52] U.S. Cl. ........................... 128/692; 128/713; 128/736
[58] Field of Search ................................. 128/692, 713, 128/673-5, 691-4, 632-15, 627

[56] References Cited

U.S. PATENT DOCUMENTS

| | | | |
|---|---|---|---|
| 3,075,515 | 1/1963 | Richards | 128/2.05 |
| 3,359,974 | 12/1967 | Khalil | 128/2.05 |
| 3,595,079 | 7/1971 | Grahn | 73/204 |
| 3,634,924 | 1/1972 | Blake et al. | 29/447 |
| 3,720,199 | 3/1973 | Rishton et al. | 128/1 D |
| 3,746,003 | 7/1973 | Blake et al. | 128/349 |
| 3,790,910 | 2/1974 | McCormack | 235/151.3 |
| 3,798,967 | 3/1974 | Gieles et al. | 73/204 |
| 3,995,623 | 12/1976 | Blake et al. | 128/2.06 |
| 4,073,287 | 2/1978 | Bradley et al. | 128/2 R |
| 4,089,336 | 5/1978 | Cage et al. | 128/303.1 |
| 4,091,813 | 5/1978 | Shaw et al. | 128/303.14 |
| 4,185,632 | 1/1980 | Shaw | 128/303.1 |

(List continued on next page.)

FOREIGN PATENT DOCUMENTS

| | | |
|---|---|---|
| 0 221 357 | 5/1987 | European Pat. Off. |
| 0 235 811 | 9/1987 | European Pat. Off. |
| 0 303 757 | 2/1989 | European Pat. Off. |
| 0 378 234 | 7/1990 | European Pat. Off. |
| 0 417 781 | 3/1991 | European Pat. Off. |
| 8505475 | 5/1985 | WIPO |
| WO91/03208 | 3/1991 | WIPO |

OTHER PUBLICATIONS

"Transtracheal Doppler: A New Procedures for Continuous Cardiac Output Measurement", Abrams et al, *Anesthesiology*, vol. 70, No. 1, Jan. 1989, pp. 134–138.

"A Thermoelectric Blood Flow Recorder in the Form of a Needle", Gibbs, 1933, vol. 41, pp. 141–146.

"Measurement of Cardiac Output in Anaesthetized Animals By a Thermo–Dilution Method", Fegler, *Quarterly Journal of Experimental Physiology*, 195, vol. 39, pp. 153–164.

(List continued on next page.)

*Primary Examiner*—Robert L. Nasser
*Attorney, Agent, or Firm*—Oblon, Spivak, McClelland, Maier & Neustadt; Bruce Canter

[57] ABSTRACT

A catheter assembly having a catheter (100) with at least one transducer (110) associated therewith for directly measuring physiological parameters of a patient or measuring an amount of a parameter indicative of a physiological condition of the patient and a memory (102) which resides at a predetermined location on said catheter (100). The memory (102) contains encoded calibration information for calibrating the transducers (110) and encoded patient specific information which can be accessed by an external processing system to which the catheter assembly is connected for processing. The memory (102) is further designed such that disconnection of the catheter assembly from the external processing system does not cause values stored in the memory to be lost so that the patient specific information need be reentered into the memory when the catheter assembly is reconnected to the same or another external processing system. By so providing the catheter assembly with memory (102), information for factory calibration, patient calibration and historical patient data may be stored with the catheter (100) for ease of use. The data in the memory (102) may also be coded to prevent easy replication of the catheter (100) by a competing manufacturer.

64 Claims, 3 Drawing Sheets

U.S. PATENT DOCUMENTS

| | | | |
|---|---|---|---|
| 4,198,957 | 4/1980 | Cage et al. | 128/1 R |
| 4,199,816 | 4/1980 | Humphrey | 364/571 |
| 4,206,759 | 6/1980 | Shaw | 128/303.1 |
| 4,207,896 | 6/1980 | Shaw | 128/303.1 |
| 4,209,017 | 6/1980 | Shaw | 128/303.1 |
| 4,236,527 | 12/1980 | Newbower et al. | 128/692 |
| 4,240,441 | 12/1980 | Khalil | 128/692 |
| 4,303,984 | 12/1981 | Houvig | 364/571 |
| 4,364,390 | 12/1982 | Shaw | 128/303.1 |
| 4,399,823 | 8/1983 | Donnelly | 128/736 |
| 4,407,298 | 10/1983 | Lentz et al. | 128/713 |
| 4,418,392 | 11/1983 | Hata | 364/571 |
| 4,446,715 | 5/1984 | Bailey | 73/1 R |
| 4,481,804 | 11/1984 | Eberhard et al. | 73/1 G |
| 4,499,547 | 2/1985 | Inuiya et al. | 364/571 |
| 4,499,907 | 2/1985 | Kallok et al. | 128/786 |
| 4,507,974 | 4/1985 | Yelderman | 73/861.06 |
| 4,524,264 | 6/1985 | Takeuchi et al. | 219/497 |
| 4,572,206 | 2/1986 | Geddes et al. | 128/692 |
| 4,576,182 | 3/1986 | Norman | 128/692 |
| 4,611,304 | 9/1986 | Butenko et al. | 364/571 |
| 4,621,643 | 11/1986 | New, Jr. et al. | 128/633 |
| 4,632,125 | 12/1986 | Webler et al. | 128/692 |
| 4,671,295 | 6/1987 | Abrams et al. | 128/663 |
| 4,684,245 | 8/1987 | Goldring | 356/41 |
| 4,685,470 | 8/1987 | Sekii et al. | 128/692 |
| 4,700,708 | 10/1987 | New, Jr. et al. | 128/633 |
| 4,708,777 | 11/1987 | Kuraoka | 204/1 T |
| 4,718,423 | 1/1988 | Willis et al. | 128/634 |
| 4,722,347 | 2/1988 | Abrams et al. | 128/663 |
| 4,733,669 | 3/1988 | Segal | 128/663 |
| 4,759,378 | 7/1988 | Swendson et al. | 128/786 |
| 4,770,179 | 9/1988 | New, Jr. et al. | 128/633 |
| 4,785,823 | 11/1988 | Eggers et al. | 128/692 |
| 4,796,640 | 1/1989 | Webler | 128/736 |
| 4,814,586 | 3/1989 | Grise | 219/549 |
| 4,819,655 | 4/1989 | Webler | 128/713 |
| 4,832,504 | 5/1989 | Hori et al. | 374/183 |
| 4,841,981 | 6/1989 | Tanabe et al. | 128/692 |
| 4,856,530 | 8/1989 | Vandervelden | 128/692 |
| 4,858,615 | 8/1989 | Meinema | 128/668 |
| 4,868,476 | 9/1989 | Respaut | 73/618 |
| 4,869,263 | 9/1989 | Segal et al. | 128/692 |
| 4,901,734 | 2/1990 | Griffin et al. | 128/692 |
| 4,941,475 | 7/1990 | Williams et al. | 128/692 |
| 4,942,877 | 7/1990 | Sakai et al. | 128/633 |
| 4,947,852 | 8/1990 | Nassi et al. | 128/662 |
| 4,951,682 | 8/1990 | Petre | 128/713 |
| 4,954,318 | 9/1990 | Yafuso et al. | 422/59 |
| 5,007,423 | 4/1991 | Branstetter et al. | 128/633 |
| 5,009,234 | 4/1991 | Alt | 128/672 |
| 5,046,505 | 9/1991 | Sekii et al. | 128/713 |
| 5,047,025 | 9/1991 | Taylor et al. | 606/31 |
| 5,056,526 | 10/1991 | Khalil | 128/692 |
| 5,080,106 | 1/1992 | Sekii et al. | 128/692 |
| 5,121,749 | 6/1992 | Nassi et al. | 128/692 |
| 5,158,082 | 10/1992 | Jones | 128/633 |
| 5,214,267 | 5/1993 | Hoshi et al. | 219/497 |
| 5,217,019 | 6/1993 | Hughes | 128/668 |
| 5,261,411 | 11/1993 | Hughes | 128/668 |
| 5,277,191 | 1/1994 | Hughes | 128/692 |
| 5,383,874 | 1/1995 | Jackson et al. | 606/41 |

OTHER PUBLICATIONS

"Studies on the Destruction of Red Blood Cells", Ham et al, *Blood*, vol. 3, 1948, pp. 373–403.

"Thin Film Thermistors", Morris et al, *Journal of Physics Engineering: Scientific Instruments*, vol. i, 1975, pp. 411–414.

"Shape and Shape Transformations of Heated Human Red Cells", Ponder, *J. Exp. Biol.*, vol. 26, 1950, pp. 35–45.

"Instantaneous and Continuous Cardiac Output Obtained with a Doppler Pulmonary Artery Catheter" Segal et al. *Experimental Studies*, JACC vol. 13, No. 6, May 1989, pp. 1382–1392.

"The Influence of Temperature on Red Cell Deformability", Williamson et al., *Blood*, vol. 46, No. 4 Oct. 1975, pp. 611–624.

"The Output of the Heart in dogs", Stewart, *The American Journal of Physiology*, vol. 57, 1921, pp. 27–50.

A Continuous Cardiac Output Computer Based on Thermodilution Principles, R.A. Normann et al., Annals of Biomedical Eng., vol. 17, pp. 61–73, 1989.

Investigation of a Continuous Heating/Cooling Technique for Cardiac Output Measurement, Kevin C. Ehlers et al., Annals of Biomecial Eng., vol. 15, pp. 551–565, 1987.

Cardiac Output Estimation by a Thermodilution Method Involving Intravascular Heating and Thermistor Recording, T. Barankay et al., Acta Physiologica Academiae Scientiarum Hungaricae, Tomus 38(2–3), pp. 167–173, 1970.

Measurement of Cardiac Output by Thermal–Dilution and Direct Fick Methods in Dogs, H. H. Khalil et al., Journal of Appl. Physiol., vol. 21(3), pp. 1131–5 1966.

Determination of Cardiac Output in Man by a New Method Based on Thermodilution, H. H. Khalil et al., Preliminary Communications, Jun. 22, 1963, pp. 1352–4.

Repeated or Continual Measurements of Cardiac Output in the Squirrel Monkey (Saimiri sciureus) by Thermodilution, H. H. Khalil, Bureau of Med. and Surgery, MR011.01.4, Naval Aerospace Med Inst., Mar. 8, 1968.

CRC Handbook of Chemistry and Physics, 60th Ed., 1979–1980, p. E–85 Cole–Parmer Instrument Co., Niles, I1, (Catalog pp. 1259–61).

Baxter healthcare Corp., (Catalog pp. 1, 2, 5 and 6) Jun. 1992 Service Manual for Model COM–1 Thermodilution Cardiac Output Computer, American Edwards Laboratories, Jun. 1984, p. 6, Table 2.1.

"Continuous Thermal Measurement of Cardiac Output", Philip et al, *Transactions on Biomedical Engineering*, vol. SME–31, No. 5, May 1984, pp. 393–400.

DIAGNOSTIC CATHETER WITH MEMORY

CROSS-REFERENCE TO RELATED APPLICATIONS

This patent application is a continuation-in-part application of U.S. patent application Ser. No. 07/769,536 to Quinn et al., filed Oct. 1, 1991, now abandoned, which was originally a continuation-in-part application of U.S. patent application Ser. No. 07/647,578 to Quinn et al., filed Jan. 29, 1991 now abandoned. This patent application is also a continuation-in-part application of U.S. patent application Ser. No. 08/049,321 to Quinn et al., filed Apr. 19, 1993, which is a continuation application of U.S. patent application Ser. No. 07/647,578 to Quinn et al., filed Jan. 29, 1991, now abandoned, and which is hereby incorporated by reference as is if fully set forth herein.

BACKGROUND OF THE INVENTION

1. Field of the Invention

The present invention relates to a diagnostic catheter for insertion into the bloodstream of a patient, and more particularly, to a diagnostic catheter with an integral memory device which contains factory calibration and factory identification information, software program segments, patient specific calibration information, historical information and the like which is not lost when the catheter is disconnected from its associated display device.

2. Description of the Prior Art

Diagnostic catheters have been constructed in various configurations and used in medicine for a multitude of purposes. Such catheters are designed to reside within lumens, chambers, orifices and tissues of various organs, including arteries, veins, the heart and the like. Medical catheters have been used as conduits to either infuse fluids or drugs or as conduits for connecting intra-vascular or organ fluids to transducers for measuring pressure, flow, temperature, oxygen saturation and the like. Catheters have also been used to assist in blood circulation as described, for example, by Rishton et al. in U.S. Pat. No. 3,720,199, which relates to an intra aortic balloon catheter assembly which is implanted in the descending aorta and connected to instrumentation to inflate/deflate the balloon synchronously with the cardiac cycle.

Medical catheters also have been constructed such that transducers can be mounted directly on the catheter, either at the tip, on the surface, or within the catheter body, for measuring physiologic parameters and sending the information directly to a monitor or display device. Such transducers include catheter mounted thermistors for measuring temperature, pressure transducers for measuring hydrostatic pressure, and oximeters for measuring blood oxygen saturation.

However, for particular catheter-mounted transducers, certain errors are present. Some errors are inherent in the design of the transducer; some are caused by variations in the transducer as a result of manufacturing processes; some are caused by changes in the transducer due to aging or use; and some are patient specific. Although such errors can be measured, several practical problems arise. For example, although design or manufacturing errors can be measured for each individual transducer, that information must be conveyed to either the end user or to a monitor or measuring device so that the errors may be compensated. For example, Lentz et al. describe in U.S. Pat. No. 4,407,298 a connector for a thermodilution catheter which joins the catheter to an output computer. However, the device of Lentz et al. simply uses individual "bit" lines, each of which can be either open or closed so that four different coded states reflecting the size of the catheter are possible, and does not relay information about the transducers themselves to the output computer.

While Lentz et al. do not describe that information about the transducers may be contained on the catheter, other prior art catheter sensors utilize a memory unit which is connected to the sensors and to signal processing circuitry. For example, Meinema describes in U.S. Pat. No. 4,858,615 an integral sensor and memory combination unit where information regarding the characteristics of the sensor or sensor-memory combination are permanently recorded in the memory and the sensor and memory are indissolubly coupled together. The recorded information (such as data for linearizing the sensor outputs) is automatically read and retrieved by separate electronic processing circuitry. However, the system of Meinema is described only for transducers which receive naturally occurring physiological parameters and is not described for use with transducers which measure responses to energy or outputs from other introducing type transducers. In addition, Meinema corrects the transducer responses for both amplitude and offset and is concerned only with displaying a corrected physiological parameter. As a result, Meinema does not consider correcting or modifying the transducer for calculation, estimation, or computation of derived measurements. Furthermore, Meinema gives no consideration to correcting, modifying, compensating for energy, indicating or delivering substances via introduction transducers. It is thus desirable that sensor/memory systems of the type taught by Meinema be expanded to include the above-mentioned capabilities as well as other capabilities to be described in the following detailed description of the invention.

Non-catheter based measuring systems frequently have provided correcting means comprising memories for storing correction data. For example, Hata describes in U.S. Pat. No. 4,418,392 a measuring device having a measurement correcting module with a memory unit for storing correction data which is used to correct digitized transducer data. However, this system requires the measured data to be altered at the analog to digital converter. It is desired that such modifications of the raw data be avoided to ensure accuracy. Similarly, Bailey describes in U.S. Pat. No. 4,446,715 using correcting means responsive to calibration means for correcting the measured physical variable. This is done for pressure transducers which are not catheter based by using information from a ROM (Read Only Memory) to correct the transducer output without any incorporation of the information into a microprocessor program. However, as with the system of Hata, this system requires the raw data to be modified.

Other disclosures directed to calibration of non-catheter-based sensors using a memory device include U.S. Pat. No. 4,481,804 to Eberhard et al.; U.S. Pat. No. 4,499,547 to Inuiya et al.; U.S. Pat. No. 4,611,304 to Butenko et al.; U.S. Pat. No. 4,868,476 to Respaut; and U.S. Pat. No. 4,942,877 to Sakai et al. New, Jr. et al. describe in U.S. Pat. Nos. 4,770,179, 4,700,708 and 4,621,643 an oximeter with a calibration system; however, this system uses a resistor to code the LED information for the pulse oximeter. Similarly, Vandervelden in U.S. Pat. No. 4,856,530 describes a calibration system using a capacitor to store the calibration information.

In addition, although errors which arise once the transducer is in use, either because of aging or other processes of the transducer or because of patient physiological variations, can be measured by in vivo or patient calibration tests, again the results must be retained by the measuring device or monitor for display to the end user. Moreover, a more serious problem is that the transducer, once inserted in a patient, cannot be removed. Rather, the inserted transducer must move with the patient. Nevertheless, when the patient is moved from one critical care environment to another, such as from the operating room to the intensive care unit, the monitoring equipment is often not moved, but rather the catheter is disconnected from the original monitor and reconnected to another monitor in the new location. Such disconnection typically results in the loss of transducer specific or patient specific information or requires the operator to re-enter the information, resulting in increased work, frustration, and reduction in quality of patient care.

Another problem for catheter manufacturers is that generally the catheter is relatively simple in proportion to the complexity of the computing, calibration and display devices, yet the profits are made from the sale of the catheters, not the monitors. As a result, even though a manufacturer may develop, manufacture, and sell the catheter and display device as a system, the catheter can be easily replicated by a competitor and manufactured and sold without the display device, resulting in a significant loss of profits for the original manufacturer. This can be somewhat prevented if the catheter and display device have some mechanism by which a competing manufacturer may be prevented from copying the catheter alone and selling it in place of the original catheter. A suitable mechanism of this type is desired.

Previous inventors have addressed this problem by designing various types of devices for encoding transducer factors for calibration. For example, Houvig in U.S. Pat. No. 4,303,984 places in a common connector a ROM, shift register and other sensor electronics powered by a power supply which is also included in the same connector. In the Houvig device, when the ROM information is desired, the information is "clocked" from the ROM and is combined or superimposed onto the raw sensor electronics. However, such an arrangement is unduly complicated and expensive for use in a diagnostic catheter of the type to which the present invention is directed. A simpler and less expensive alternative is desired.

Accordingly, it is desired to provide a catheter with memory which can overcome the above-mentioned problems by retaining the information specific to factory calibration, patient specific calibration data, historical patient data and the like. It is also desirable that this information be coded to prevent unauthorized access. The present invention has been designed to meet these needs.

SUMMARY OF THE INVENTION

The above-mentioned and other problems of the prior art are resolved in accordance with the present invention by providing a catheter apparatus with an integral memory for retaining information specific to factory calibration, patient calibration data, patient historical data, encoded data and the like. For example, a presently preferred embodiment of the invention relates to a multilumen flow directed pulmonary artery catheter which has associated therewith one or more transducers for measuring different transducer and physiological parameters of the patient when the catheter is placed in various vessels, lumens, bladders, orifices, chambers and other body spaces of the patient. Such a system is described by way of example in the aforementioned parent application for use with the processing circuitry of U.S. Pat. No. 5,146,414 to McKown et al., both of which have been assigned to the same assignee as the present invention. In accordance with the techniques set forth in these patent applications, several parameters are measured, such as temperature (using a thermistor or thermocouple), cardiac output (which requires the transfer of indicator from a transducer such as a heater filament to the flowing blood and the measurement of the response at the distal thermistor) and oxygen saturation or oximetry (which requires the transmission of two or more appropriate wavelengths of light into the blood or tissue and the detection of light reflection/ absorbance). Accordingly, preferred embodiments of the invention will be described for use with such devices.

In particular, the present invention relates to a device for gathering physiological data from a patient and supplying the gathered data to a processing system. Preferably such a device in accordance with the invention comprises at least one transducer for directly measuring physiological parameters of the patient or measuring an amount of a parameter indicative of a physiological condition of the patient, and a memory which resides at a predetermined location with respect to the at least one transducer. Preferably, the memory contains calibration information for calibrating the transducer and patient specific information which can be accessed by the processing system to which the device is connected for processing. Preferably, the memory is selected such that disconnection of the device from the processing system does not cause values stored in the memory to be lost so that the patient specific information need be reentered into the memory when the device is reconnected to the same or another processing system. Also, in order to prevent piracy, it is preferred that the stored data be encoded.

Preferably, the device of the invention is a catheter assembly and the transducers are disposed on or about the catheter. The memory of the invention may be disposed at different locations within the catheter assembly. For example, the memory may be disposed within the body of the catheter, in an area adjacent one of the transducers or in a connector connected to a proximal end of the catheter assembly for allowing at least one transducer of the catheter to communicate with the processing system, which may be a conventional external processing system or computer. Such a connector preferably comprises leads which are connected to the memory so as to allow access to contents of the memory by the external processing system connected to the catheter.

The catheter of the invention may be of different types and may include transducers of different types. For example, the catheter may be designed for single patient use or multiple patient use. Also, the transducers of the catheter preferably comprise a first transducer for introducing energy or a physical indicator into a physiological medium of the patient and a second transducer for directly measuring physiological parameters of the physiological medium in response to the energy or physical indicator which has either passed through the physiological medium or passed directly from the first transducer to the second transducer.

In a particular embodiment, the first transducer may be a heating element and the second transducer may be either a thermistor or a thermocouple for measuring temperature changes in the physiological medium caused by the heating element. In this embodiment, the heating element is preferably made of a thin, flexible material which may be wrapped either on the exterior of the catheter body wall and then covered by an external sheath material so that the heating element material is not exposed to the blood or on the outer surface of a supporting sheath inserted into the catheter lumen. During use, the heating element temperature is preferably measured simultaneously with the thermodilution measurement without the use of a second measuring transducer. The heating element temperature is not measured to calculate velocity, but rather to insure that a safe heating element temperature may be maintained. This is accomplished in one embodiment by forming the heating element of a material which has a resistance proportional or inversely proportional to its temperature.

On the other hand, the first transducer may supply thermal energy, ultrasound or electromagnetic energy to the physiological medium and the effects thereof on the physiological medium may be measured by the second transducer for use by the external processing system to measure blood flow, cardiac output and/or flow of another physiological substance of the patient. In addition, the first transducer may supply optical energy to a physiological medium of the patient and the effects thereof on the physiological medium may be measured by the second transducer for use by the external processing system to measure oxygen saturation, oxygen tension ($PaO_2$), pH level, $PCO_2$ concentration, electrolyte concentration (e.g., sodium, potassium, chloride, bicarbonate and glucose) and the like. However, the detection transducers used in accordance with the invention may measure naturally occurring substances, parameters, or other physiological events which have not been supplemented with an energy or other type of introduction transducer such as a temperature, pressure, or ion concentration transducer. Accordingly, the technique of the invention is not limited to use with heat (temperature), optical energy or indicator type transducers.

In accordance with another aspect of the invention, the connector leads are connected such that the external processing system can write calibration information to the memory of the catheter during operation for in vivo calibration. This information may then be used during processing of the detected data to make necessary corrections or modificiations to the transducer outputs or the subsequent computations using the raw information received from the transducers.

During operation, the external processing system may access the patient specific information in the memory via the connector leads so that the memory may provide historical patient information to the external processing system for display as trending data of the patient. This information is maintained such that even when the catheter assembly is disconnected from the external processing system the patient's historical data can be later retrieved when the catheter assembly is reconnected to the same or another external processing system. For this purpose, the catheter assembly may further comprise a battery located in proximity of the memory for providing power to the memory when the memory is not connected to the external processing system. In addition, the calibration information and patient specific information are preferably encoded in accordance with a proprietary code stored in the memory. This proprietary code may then be read by the external processing system to determine whether the catheter assembly is supplied by a particular manufacturer prior to conducting further processing. Preferably, the proprietary code is a binary code stored in the memory and is accessed by the external processing system and used thereby to decode the encoded calibration information and encoded patient specific information.

In preferred embodiments of the invention, the catheter may be either an intra-arterial catheter, an intra-venous catheter, an intra-chamber catheter, an intra-orifice catheter, an intra-cavity catheter or an organ contact catheter. On the other hand, the memory of the invention may also be used in non-catheter applications such as topically applied sensors including pulse oximeters, transcutaneous oxygen electrodes and the like.

In one preferred embodiment, wherein the catheter has a heating filament and a temperature detecting means, calibrating means are provided for calibrating both the heating filament and the temperature detecting means. Preferably, the calibrating means comprises a Read Only Memory (ROM) contained within the catheter member for storing calibration information for either or both the heating filament and the temperature detecting means, as well as any other necessary information. Preferably, the ROM is located at the proximal end of the catheter and includes calibration information relating to heating filament resistance at a given temperature, heating filament heat transfer efficiency, temperature coefficient of resistance and thermistor information. Moreover, the ROM may be connected to a cardiac output computer so as to pass a program segment, stored in the ROM, of a program used by the cardiac output computer to calculate cardiac output of the patient, whereby calculation of the patient's cardiac output cannot commence until the cardiac output computer is connected to the ROM and the program segment transferred to the cardiac output computer.

In accordance with yet another aspect of the invention, the memory may further contain catheter identification information including manufacture date, batch number, sterilization date, expiration date, catheter transducer number and type, manufacturer's name and address and any other unique identification or process information. In addition, the memory may also contain a computer program, a computer program segment, a software subroutine and computer memory addresses which can be read by the external processing system and used thereby to verify, correct, or modify the processing of the catheter transducer information. In such an embodiment, the software of the catheter memory and the external processing system together form a unique software combination such that system operation cannot occur without the two software pieces together. This assures that only catheter memories programmed by particular manufacturers can be used with a particular processing system. For this purpose, the memory may further contain a proprietary code which is read to determine whether the catheter assembly is supplied by a particular manufacturer.

BRIEF DESCRIPTION OF THE DRAWINGS

The above and other objects and advantages of the invention will become more apparent and more readily appreciated from the following detailed description of the presently preferred exemplary embodiment of the invention taken in conjunction with the accompanying drawings, of which.

DETAILED DESCRIPTION OF THE PREFERRED EMBODIMENT

Figure 1:
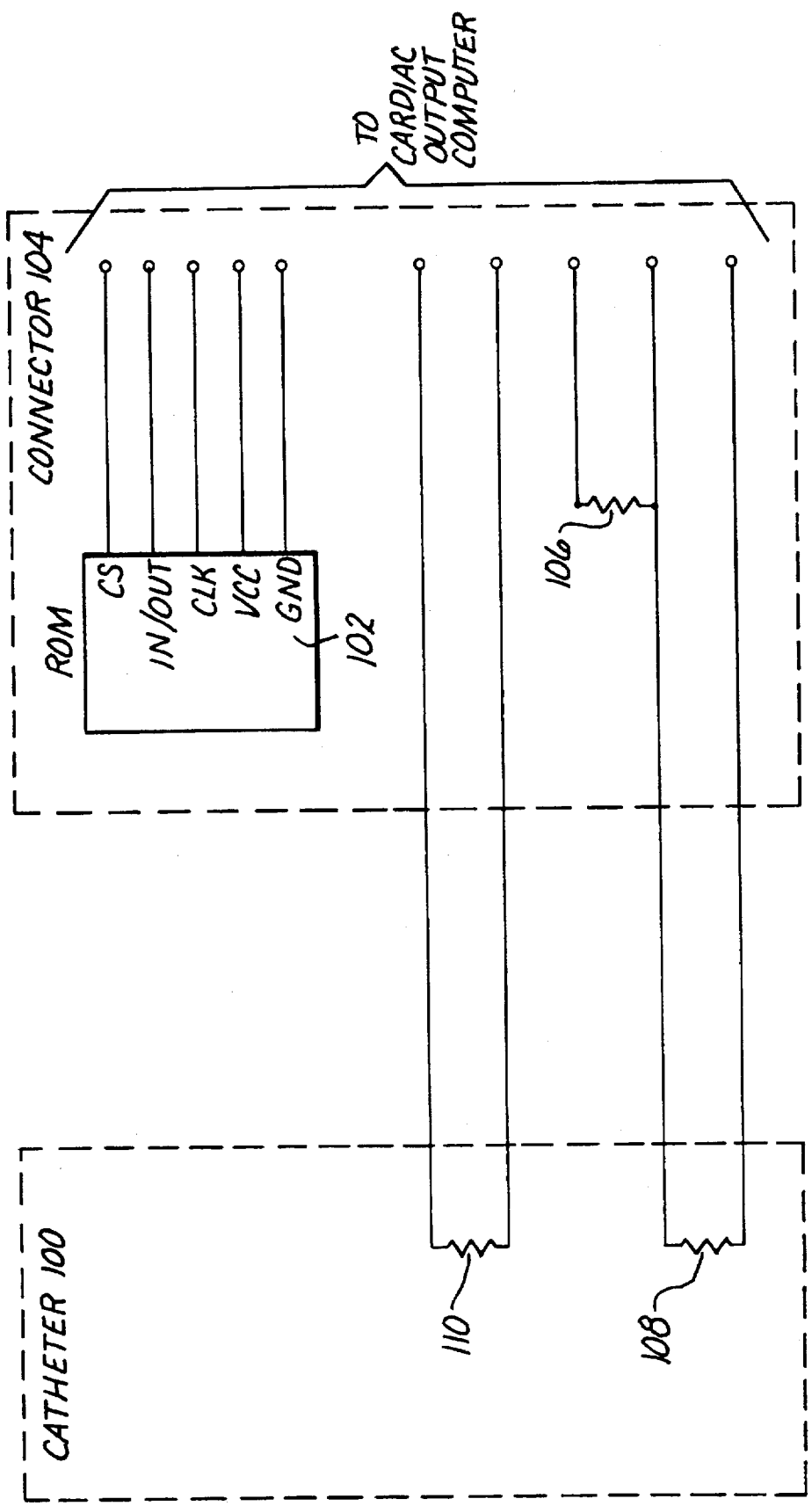
FIG. 1 illustrates a calibration circuit having a memory in accordance with a presently preferred embodiment of the invention.

A system with the above-mentioned beneficial features in accordance with presently preferred exemplary embodiments of the invention will be described below in detail with reference to FIGS. 1–5. Although the present invention is described for use with a thermodilution catheter in the preferred embodiment, it will be appreciated by those of ordinary skill in the art that the description given herein is for exemplary purposes only and is not intended in any way to limit the scope of the invention. All questions regarding the scope of the invention may be resolved by referring to the appended claims.

In a preferred embodiment, a thermodilution catheter has a heating filament which resides internal to the catheter body, either in a preformed catheter lumen or beneath an outer sheath, and which preferably does not directly contact the blood. The heating filament is preferably made of a thin, flexible material which may be wrapped either on the exterior of the catheter body wall and then covered by an external sheath material so that the heating filament material is not exposed to the blood or on the outer surface of a supporting sheath inserted into the catheter lumen. The heating filament so designed supplies a quantity of heat to the flowing blood which is used for measuring the volumetric blood flow using an indicator dilution equation. In a preferred embodiment the heating filament is comprised of a material having a high temperature coefficient of resistance, whereby resistance of the heating filament is inversely proportional to its temperature (i.e., it has a negative temperature coefficient of resistance). This aspect of the invention enables power to the heating filament to be reduced when resistance of the heating filament exceeds a predetermined resistance amount, which is reached when the temperature of the heating filament reaches approximately 52° C. A material suitable for the heating filament thus has a temperature coefficient of resistance greater than 0.001 $\Omega/\Omega$–° C. Also, such a material preferably has a low thermal capacitance and high thermal conductivity. Preferred heating filament materials include an alloy of approximately 70% nickel and 30% iron and an alloy of approximately 29% nickel, 17% cobalt and 54% iron.

During operation, since the heating filament formed as described above is used primarily to insert heat into the blood stream, it will rise to a temperature higher than the surrounding environment. Thus, it is necessary to know the filament temperature since, should the temperature become excessive, damage could result to the surrounding blood and tissues. Normally, a second temperature sensing device such as a thermistor or thermocouple would need to be embedded next to the filament to measure its temperature. However, by using a filament material which has a high temperature coefficient of resistance as herein described, not only can it be used as a heat supplier, but it can also serve as its own temperature sensing device. For example, resistance of any material is measured as follows:

$$R = \frac{\rho \cdot l}{A},$$

where
$\rho$ is the resistivity,
l is the length, and
A is the cross-sectional area.
Then:

$$\Delta R = \frac{\Delta \rho \cdot l}{A},$$

and if $\alpha$, the mean temperature coefficient of resistivity, is defined as:

$$\alpha = \frac{1}{\rho} \cdot \frac{\Delta \rho}{\Delta T},$$

where
$\Delta \rho$ is the change in the coefficient and
$\Delta T$ is the change in temperature,
then:

$$\Delta T = \Delta R \frac{A}{l \cdot \alpha \cdot \rho}.$$

Then, by measuring the current (i) and the voltage (v), both delivered power and resistance of the filament can be simultaneously measured as:

$$\frac{\Delta v}{\Delta i} = \Delta R.$$

When a thermodilution catheter in accordance with the invention is connected to a cardiac output computer via a heater connector, an electrical current is applied to the heating filament in the form of pulses. When the heating filament is activated, an approximate average of 7.5 watts of power may be delivered to the heating filament. During operation, as described above, the cardiac output computer may continuously measure and monitor the filament temperature so as to limit the peak filament temperature to a maximum of 52° C. (which corresponds to a peak surface temperature of about 48° C. and an average surface temperature of about 44° C., depending upon the material composition and thickness). For example, in the event the heating filament temperature exceeds 52° C. for more than, say, 15 seconds at full power, the delivered heating filament power is reduced. Then, if the heating filament temperature exceeds 52° C. for more than, say, 15 seconds at reduced power, the heating filament power may be shut off and a panel alarm activated. This prevents the peak surface temperature from exceeding 48° C. Moreover, the average catheter surface temperature should not exceed 44° C. since the power will be switched "ON" approximately 50% of the time. Furthermore, if the average cardiac output exceeds 3.5 liters/minute, the catheter's average surface temperature will generally remain below 44° C. Thus, regulation of power to the catheter only becomes an issue when the cardiac output becomes less than about 3.5 liters/minute. However, since the power to the heating filament is reduced or shut off as the filament temperature reaches 52° C., the heating element of the invention can be made relatively fail-safe through closed-loop control of the surface temperature.

By using a power source which is a constant voltage source, an increasing catheter filament temperature can be directly detected as an increasing filament resistance which reduces the power delivered to the heating filament. In this manner, the actual current and voltage to the catheter filament may be continuously monitored. From the values of current and voltage, a delivered power may be calculated which is needed to calculate flow, and the filament resistance may be calculated and used for computing the filament temperature. Thus, at all times, the actual filament temperature is known.

In the calculation of cardiac output using a thermodilution catheter and an associated processing system, it is necessary to know certain properties about the measuring transducer, such as a thermistor or thermocouple, and the heat application or heating filament efficiency, for in the manufacturing process it is difficult to produce either thermistors or thermocouples or heating filaments which uniformly have the same properties. Thus, to reduce the errors which would be introduced into the calculation of cardiac output due to these variances, it is necessary to calibrate or measure the physical properties of both the thermistor or thermocouple and the heating filament. Since in a clinical environment each cardiac output computer may be attached over time to various pulmonary artery catheters and to eliminate the need for the user to manually transcribe these calibration numbers to the computer, a coding technique has been developed in accordance with the invention to pass the calibration information.

Prior art thermodilution catheters and pulse oximeter sensors have used resistors to code the values for thermistors or LEDs. For example, New, Jr. et al. in the aforementioned U.S. Pat. No. 4,700,708 use a resistor to calibrate LED wavelengths on a pulse oximeter. However, the present inventors know of no previous attempt to code the filament calibration for transferring the calibration information of the heating filament solely or the calibration information of the heating filament and thermistor or thermocouple together. Thus, in accordance with the present invention, calibration of the heating element may be conducted by measuring the heater resistance at a known temperature. The catheter assembly can then use the previously calibrated thermistor or thermocouple and a built-in ohm meter to establish a calibrated reference point for the heater element. This approach has the advantage of calibrating the heater immediately prior to use in a patient at the patient's body temperature. Such an accurate calibration of heater resistance and temperature is necessary to accurately monitor heater temperature to insure patient safety.

The calibration circuit of the invention may include passive electronic components such as resistors, inductors and capacitors such that the value of the components correspond to a particular calibration value or number according to a predetermined table. On the other hand, active electronic components including numerous nonlinear components may be used such that a particular performance corresponds to a particular calibration number or value. Such calibration information is preferably stored in a memory component such as a ROM (Read Only Memory), RAM (Random Access Memory), nonvolatile memory devices or other types of volatile or nonvolatile memory or digital devices of any desired size. The calibration information preferably includes codes that represent the filament resistance, filament efficiency, and other parameters. If properly selected, one or more electronic components may be used to encode the calibration information of the thermistor or thermocouple, such as its β value, and the filament resistance, filament efficiency and other parameters.

Thus, the calibration information for both the thermistor or thermocouple and the heating filament may be encoded by one or more active or passive electronic components or these values may be stored in a suitable memory device. The cardiac output computer may then decode this information and incorporate it into the calculation of cardiac output, for example. However, this step may be eliminated if the actual appropriate software is contained in the catheter itself. For example, a memory device such as a ROM may be contained in the catheter with a portion of the software utilized by the cardiac output computer resident within it. Such information might include program segments or historical patient data. Thus, when the catheter is connected to the cardiac output computer, prior to the beginning of processing for determining the cardiac output, the software or program segment contained in the catheter memory device (ROM or RAM) may be transferred to the main software program of the cardiac output computer. This feature of the invention also provides an additional safety feature, for the cardiac output computer will not start until it has transferred the program segment and incorporated this segment into its own program.

The calibration circuitry of the type just described can be seen by way of example in FIG. 1. As should be apparent to one of ordinary skill in the art, the calibration circuit of FIG. 1 is quite different from that used in typical prior art thermodilution catheters. In particular, classic thermodilution catheters use calibration resistances which are connected to form one-half of a bridge circuit with the thermistor or thermocouple. In such devices, the reference resistor is selected to match the thermistor or thermocouple for a standard temperature. In this manner, compensation for variability in the thermistors or thermocouples may be achieved. However, by using the calibration circuit of the invention whereby a RAM or ROM containing calibration data is included within the connector of the catheter, such a reference resistor for calibration purposes is not needed. Such a memory for use with a thermodilution catheter 100 is shown as memory 102 of connector 104 in FIG. 1.

Preferably, the software module referred to above is stored in the memory 102 and includes such things as the format version for the calibration data, trademark information, historical patient data (such as cardiac output for the previous several hours) or whatever information is desired for controlling the cardiac output program. Thus, by placing the encoded calibration data within the memory 102 and placing the memory 102 on the catheter 100, the reference resistance 106 for the thermistor or thermocouple 108 may be eliminated. In addition, only a catheter having a memory 102 storing the necessary information for operating the program of the cardiac output computer may be used in conjunction with the cardiac output computer to obtain the desired calculation.

Thus, the purpose of the present invention as illustrated in FIG. 1 is to disclose a method of enhancing the performance of a catheter or catheters such as those described in the aforementioned related application by retaining factory calibration, factory identification, computer or monitor specific software program segments, patient specific calibration information, and patient historical information in the catheter which is not lost when the catheter is disconnected from the computer, monitor or other display device, as when the patient is moved.

In particular, the catheter of the invention contains in the body, connector, or some other aspect of the catheter a memory 102 which can be accessed by any of a variety of means when the catheter is connected to an external processing device such as a cardiac output computer. The memory 102 is either of a volatile or nonvolatile type such that when the memory 102 is not connected to the external processing device the memory contents are not lost. In addition, the external processing device is preferably allowed, when connected to the catheter 100 and consequently to the memory 102, to address any byte of the memory 102 and to either read or write to the byte at that address. In addition, the relevant information can be written to the appropriate address of the memory 102 during the portion of the manufacturing process during which the calibration data is measured.

In a preferred embodiment of the invention, different segments of the memory 102 may contain any or all of the following information segments:

1. A catheter unique serial number;
2. Manufacturing identification data, such as calibration, manufacture, sterilization and ship date or any other date and time information relevant to the catheter 100;

3. A software program segment which is not integral to the catheter 100 or to any aspect of the catheter 100 or catheter transducer 110, but is instead program information, such as a subroutine, which is incorporated into the software program of the display device;
4. A unique security code which allows the monitor to identify a catheter which has been manufactured by the manufacturer of the monitor or a competing manufacturer; and
5. Manufacture or calibration information about the energy introduction transducer 110 which is the part of the catheter 100 used to introduce energy into the flowing blood for the thermodilution measurement. Such information could contain, for example, filament or transducer nominal electrical resistance, heat transfer coefficient, thermal mass, filament composition and coefficient of resistance.

Of course, in view of the present disclosure, those skilled in the art will appreciate that other desirable information may be kept in the memory 102 as well.

The present invention will now be described in more detail with respect to FIGS. 2–5.

Figure 2:
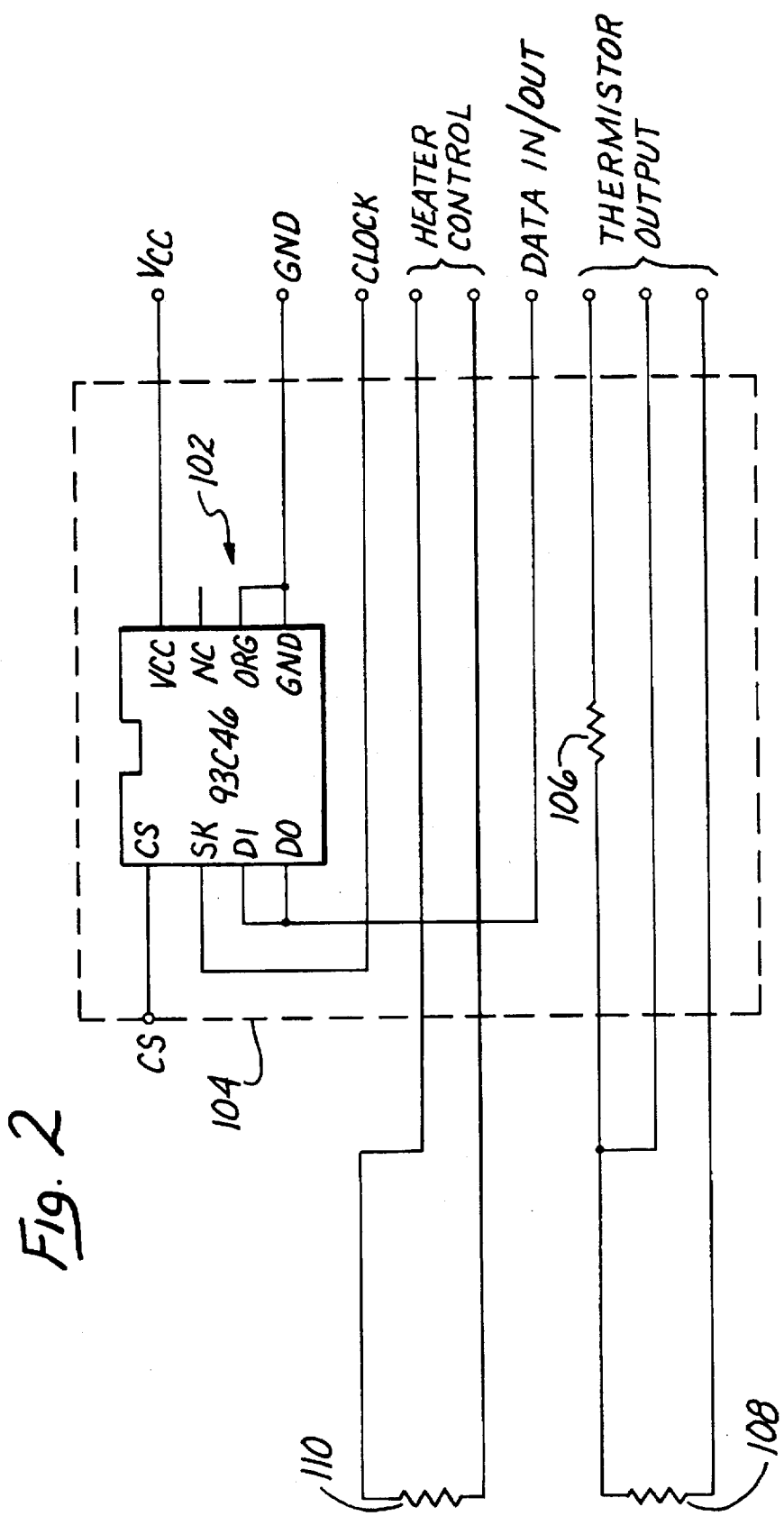
FIG. 2 illustrates in more detail the connections of the memory of FIG. 1 for the case where the memory is a CAT93C46 1 Kbit Serial EEPROM.

FIG. 2 illustrates a schematic for a catheter memory 102 in accordance with a preferred embodiment of the invention. As shown, a standard thermistor/resistor bridge catheter assembly having reference resistor 106 and thermistor 108 may be used as in the embodiment of FIG. 1 to measure blood temperature. Catheter memory 102 is also provided and is connected as shown to include voltage supply lines (VCC), clock lines (SK), data lines (DI and DO), and a ground (GND). In the presently preferred embodiment, a CAT93C46 1 Kbit serial EEPROM is used as memory 102 and is connected as shown, where CS indicates "chip select", NC indicates "no connection" and ORG indicates "memory organization". As would be apparent to one skilled in the art, although only one address or "clock line" is shown, any number of lines can be used. Also, as shown in more detail in FIGS. 3 and 4, the address and data lines preferably go to a connector 300, and these address and data lines may be shared with other transducer's lines, which in the case illustrated are filament heater lines.

Figure 3:
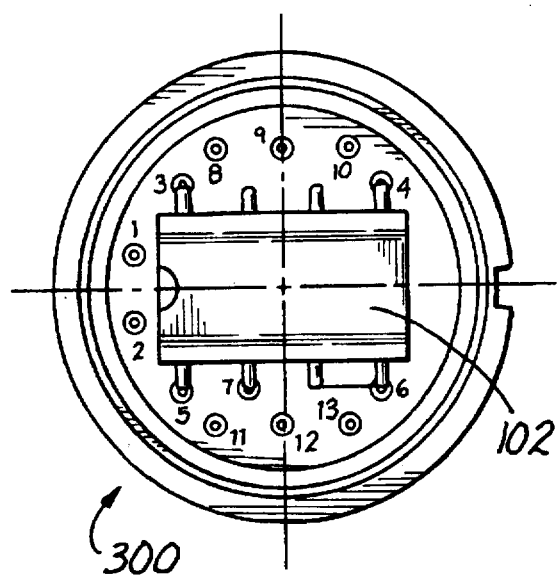
FIG. 3 and 4 respectively illustrate top and side views of the catheter connector assembly at the proximal end of a catheter having a memory in accordance with the invention.
Figure 4:
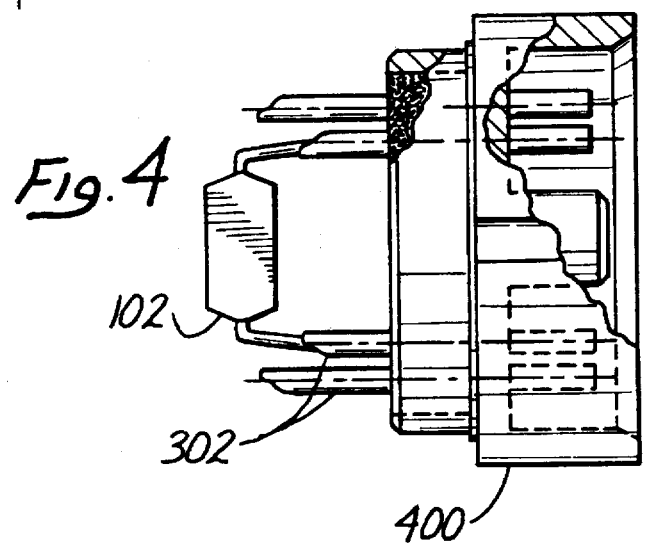
Figure 5:
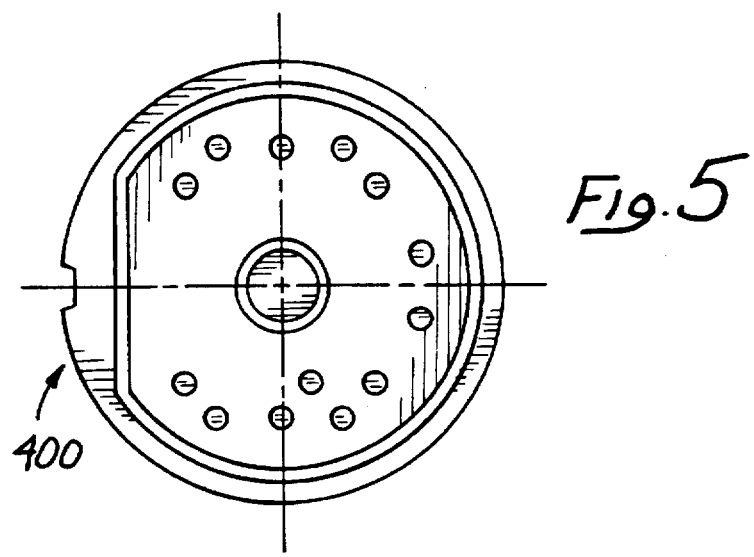
FIG. 5 illustrates an end view of a connector cover for covering the catheter connector assembly shown in FIG. 3.

FIGS. 3–5 illustrate in more detail the catheter connector 300 of the invention. As shown, the memory or chip 102 is mounted in the proximal end of the catheter at the connector 300. Connector pins 302 are attached to the pins of the memory chip 102 so as to allow the memory 102 to be accessed by an external processing device when the catheter connector 300 is plugged into the external processing device either directly or via a connecting cable. The catheter assembly may further include a connector cover 400 as shown in FIGS. 4 and 5 to protect the memory chip 1 102 from damage.

As noted above, in a preferred embodiment of the invention the memory 102 is a CAT93C46 1 Kbit serial EEPROM. A CAT93C46 memory device is organized in 64 registers of 16 bits (ORG pin at VCC) or 128 registers of 8 bits each (ORG pin at GND). Each register can be written or read serially by using the DI or DO pins. The CAT93C46 memory device is desirable since it is a CMOS EEPROM with floating gates, operates at 700 Khz, and is designed to endure 10,000 erase/write cycles and a data retention of 10 years. However, those skilled in the art will realize that other memory devices will satisfy the characteristics of the present invention.

The allocation and use of memory 102 will now be described. In particular, the algorithm used to encode and decode the data stored in the EEPROM of several models of thermodilution catheters will be described.

As noted above, the purpose of encoding the data in the catheter EEPROM is to make it more difficult to copy or counterfeit the catheters in which the present invention is used, such as the catheters described in the parent application. For this purpose, an algorithm is used to encode selected bytes of data within the catheter EEPROM. For example, in a preferred embodiment the first two (2) bytes of data in the EEPROM need not be encoded. This allows the software of the external processing device to read the security code in those bytes. This code is the basis of an encrypting/decrypting key for the remainder of the stored data. Several other bytes also need not be encoded (such as bytes 02 through 07) and preferably contain product information such as model number and serial number and the like which may also be read by the software of the external processing device. The remaining bytes are encoded and are initialized to contain the manufacturer's copyright notice and checksums (arithmetic 8-bit sums) which may be used by the security algorithm as shown in TABLE 1 below.

The following algorithm is preferably utilized to encode or decode the stored data. First, the security code is read from bytes 00 and 01. This code may be, for example, 0314 Hex, but any 16-bit value is possible. The checksum in byte 127 is then read and ANDed with the security code. This result is then ANDed with the complement of the security code and shifted right four places. This forms the encryption/decryption key. The data to be encrypted or decrypted is exclusive-ORed, on a word basis, with the key. The above may be illustrated by a simple C code expression as follows:

data ^=((security_code & cksum) & ~security_code)>>4;

Also, the information related to factory calibration of the catheter filament is preferably stored and read from byte 08. Of course, those skilled in the art will readily appreciate that many other types of known encoding schemes may be used. For example, the proprietary code may also be encrypted in accordance with the invention.

The data in a preferred embodiment of memory 102, after initialization, will thus appear as follows:

TABLE 1

| Byte | Function |
| --- | --- |
| 00–01 | Unencoded security code |
| 02–05 | Unencoded serial number |
| 06 | Unencoded layout byte |
| 07 | Unencoded model number |
| 08 | Encoded heater resistance |
| 09–32 | Encoded remaining data |
| 33 | Encoded checksum of above data |
| 34 | Zero byte |
| 35–38 | Longword, number of seconds since 1/1/70 |
| 39 | Checksum of all above bytes |
| 40–41 | Zero bytes |
| 42–82 | "Copyright (c) 1991 Interflo Medical, Inc." |
| 83 | Zero byte |
| 84–126 | Random uninitialized data bytes |
| 127 | Checksum of all above 127 bytes |

Then, for example, the data in the EEPROM, after patient data has been collected, will appear as follows:

TABLE 2

| Byte | Function |
| --- | --- |
| 34–35 | Patient Weight |
| 36–37 | Patient Height |
| 38 | Reserved |
| 39 | Checksum of above five (5) bytes |
| 40–43 | Timestamp of 1st CO data point |

TABLE 2-continued

| Byte | Function |
|---|---|
| 44–45 | Count of all CO data points in EEPROM |
| 46–109 | Last 64 CO data points at 15 minute intervals |
| 110 | Reserved |
| 111 | Checksum of bytes 40 through 110 |

This data is the "historical patient data" in a preferred embodiment, although other data may of course be collected.

After manufacture of the catheter assembly of the invention, the memory 102 may be accessed by an appropriate device to determine if the code stored in the memory 102 is the proper code. If this code is not the proper code, then it is known that the catheter assembly being checked is faulty or is an unauthorized copy. The tester then may choose to render the tested catheter non-functional or temporarily or permanently inoperative through any of a variety of means. In this manner, a mechanism is provided to insure that the catheter assembly being used is not an imitation catheter and to prevent such a catheter assembly from being inserted into the patient and connected to the monitor.

As described above, the information in the memory 102 is accessible and changeable by the external computing, calculation, display, or monitoring means in the field during clinical use. However, before the catheter memory 102 leaves the factory, some of information is preferably written to the catheter memory 102 including catheter and/or transducer test, calibration, or date information.

Although an exemplary embodiment of the invention has been described in detail above, those skilled in the art will readily appreciate that many additional modifications are possible in the exemplary embodiment without materially departing from the novel teachings and advantages of the invention. For example, the memory 102 may have a small battery backup located on the connector 300 with the memory chip. Also, the memory 102 may be of any desired size and may be read only or read/write memory. In addition, the memory may be used alone or in combination with a variety of other components such as multiplexers, capacitors, resistors, operational amplifiers and the like and may be used in non-catheter applications such as pulse oximeters, transcutaneous oxygen electrodes and the like. The memory 102 also may be combined directly with other electronic components such as amplifiers, resistors, capacitors, inductors, other memory units, multiplexers, shift registers, batteries, and the like and further may be combined either directly or through the connector leads to any or all catheter transducers. Furthermore, the memory 102 may reside on a removable sensor probe that fits within a lumen of the catheter or may be included in the catheter or connector in such a way that it is accessible not directly by the external processing system but rather by means of one of the internal transducers.

Accordingly, all such modifications are intended to be included within the scope of this invention as defined in the following claims.

We claim:

1. A thermodilution catheter assembly for use in determining a patient's cardiac output, comprising:
   (i) a catheter adapted to be inserted into a patient's bloodstream, said catheter having a heating filament made of a thin, flexible material having a temperature coefficient of resistance of at least 0.001 ohms per ohm-degree centigrade; and
   (ii) a memory which resides at a predetermined location on or about said catheter, said memory storing thermodilution information comprising
      (a) heating filament calibration information, said heating filament calibration information comprising
         (1) heating filament electrical resistance of said heating filament at a given temperature,
         (2) heating filament heat transfer efficiency of said heating filament, and
         (3) heating filament temperature coefficient of resistance of said heating filament.

2. The thermodilution catheter assembly of claim 1, wherein
   said thermodilution information further comprises
      (b) a proprietary code, said heating filament calibration information that is stored in said memory is stored in said memory as encoded heating filament calibration information in an encoded form that is based upon said proprietary code such that said encoded heating filament calibration information can be decoded using said proprietary code, and
   said catheter is adapted so that said memory is readable and decodable by the external processing system.

3. The thermodilution catheter assembly of claim 2, wherein
   said memory stores said proprietary code in the form of a proprietary binary code,
   said catheter and said memory being adapted so that said proprietary binary code is accessible by the external processing system and
   said proprietary binary code and said encoded heating filament calibration information are interrelated so that said encoded heating filament calibration information is decodable using said proprietary binary code, by the external processing system.

4. The thermodilution catheter assembly of claim 1, wherein said predetermined location is within said catheter.

5. The thermodilution catheter assembly of claim 1, wherein said predetermined location is adjacent said heating filament.

6. The thermodilution catheter assembly of claim 1, wherein said catheter assembly has a proximal end and a distal end,
   said catheter assembly further comprising
      (iii) a connector at said proximal end of said catheter assembly, said connector being electrically connected to said heating filament, said connector being adapted to connect to the external processing system so that said heating filament can communicate with the external processing system, and
   wherein said predetermined location is at said connector.

7. The thermodilution catheter assembly of claim 6, wherein said connector comprises electrical leads which are connected to said memory, said electrical leads and said connector are functionally interrelated to enable access through said connector via said electrical leads to said encoded heating filament calibration information and said proprietary code that are stored in said memory.

8. The thermodilution catheter assembly of claim 7, wherein
   said connector is functionally interrelated to said memory via said electrical leads and
   said connector is structured so that thermodilution information can be written into said memory via said leads by electrical signals received by said connector while said connector receives thermodilution signals from said catheter, thereby enabling in vivo calibration.

9. The thermodilution catheter assembly of claim 1, wherein said catheter assembly further comprises one of a thermistor and a thermocouple mounted on said catheter for measuring temperature changes in the patient's bloodstream caused by heat generated in said heating filament.

10. The thermodilution catheter assembly of claim 9, wherein said heating filament is adapted to supply thermal energy to the patient's bloodstream and the thermistor or thermocouple is adapted to measure the effects of thermal energy supplied to the patient's bloodstream, for use by the external processing system to calculate one of blood flow of the patient and cardiac output of the patient.

11. A thermodilution catheter assembly system for calculating a patient's cardiac output, comprising:
   (A) a catheter assembly comprising
      (i) a catheter adapted to be inserted into the patient's bloodstream, said catheter having a heating filament made of a thin, flexible material having a temperature coefficient of resistance of at least 0.001 ohms per ohm-degree centigrade;
      (ii) a memory which resides at a predetermined location on or about said catheter, said memory storing encoded thermodilution information comprising
         (a) heating filament calibration information, said heating filament calibration information comprising
            (1) heating filament electrical resistance of said heating filament at a given temperature,
            (2) heating filament heat transfer efficiency of said heating filament, and
            (3) heating filament temperature coefficient of resistance of said heating filament; and
   (B) an external processing system which is connectable to said catheter assembly so that the external processing system can communicate with said memory and said heating filament, said external processing system comprising
      (i) means for decoding said encoded heating filament calibration information stored in said memory for generating decoded heating filament calibration information and
      (ii) means for calculating cardiac output using said decoded heating filament calibration information.

12. The thermodilution catheter assembly system of claim 11, wherein said catheter assembly further comprises:
   (iii) means, mounted to said catheter and coupled to said external processing system, for measuring resistance of said heating filament and said catheter assembly system further comprises
   (C) means, coupled to said external processing system and said heating filament, for controlling the temperature of said heating filament based upon said resistance of said heating filament and the decoded calibration information.

13. The thermodilution catheter assembly system of claim 12 wherein said means for controlling the temperature includes means for reducing electrical power transmitted to said heating filament when the resistance of said heating filament exceeds a predetermined resistance value.

14. The thermodilution catheter assembly system of claim 11, further comprising a battery located in proximity of said memory for providing power to said memory when said memory is not connected to said external processing system.

15. The thermodilution catheter assembly system of claim 11, wherein
said memory is adapted to be used with means for encoding calibration information in accordance with a proprietary code and to be written into with encoded calibration information encoded in accordance with said proprietary code and
said memory being further adapted to be read by said external processing system and used thereby to decode said encoded calibration information.

16. The thermodilution catheter assembly system of claim 15, wherein
said memory comprises means to store said proprietary code in the form of a proprietary binary code and
said memory and said catheter assembly are adapted so that said memory can be accessed by said external processing system and used thereby to decode said encoded calibration information.

17. The thermodilution catheter assembly system of claim 11, wherein said catheter assembly has a distal end and a proximal end, and
said catheter assembly further comprising
   (iii) an electrical connector electrically connected to said heating filament and at said proximal end of said catheter assembly for enabling said heating filament to communicate with said external processing system, wherein said predetermined location is at said connector.

18. The thermodilution catheter assembly system of claim 17, wherein
said connector comprises electrical leads which are electrically connected to said memory and
said connector and said memory are functionally interrelated by said electrical leads to enable access to said encoded thermodilution information stored in said memory by said external processing system.

19. The thermodilution catheter assembly system of claim 18, wherein said electrical leads are electrically connected to said memory such that said external processing system can write calibration information for either said patient or said heating filament to said memory, for in vivo calibration.

20. The thermodilution catheter assembly system of claim 11, wherein said catheter assembly further comprises one of a thermistor and a thermocouple for measuring temperature changes in the patient's bloodstream caused by heat generated in said heating filament.

21. The thermodilution catheter assembly system of claim 20, wherein
said heating filament is adapted to supply thermal energy to the patient's bloodstream and
the thermistor or thermocouple is adapted to measure the effects of the thermal energy supplied to the patient's bloodstream by heat generated in said heating filament,
said external processing system is adapted to calculate one of blood flow and cardiac output of said patient based upon measurements by said thermistor or thermocouple of said effects of the thermal energy supplied to the patient's bloodstream.

22. A thermodilution catheter assembly system for calculating a patient's cardiac output, comprising:
   (A) a catheter assembly having a distal end and a proximal end and comprising
      (i) a catheter adapted to be inserted into the patient's bloodstream, said catheter having a heating filament made of a thin, flexible material having a temperature coefficient of resistance of at least 0.001 ohms per ohm-degree centigrade; and
      (ii) a memory which resides at a predetermined location on or about said catheter, said memory storing encoded thermodilution information comprising (a) heating filament calibration information, said heating filament calibration information comprising
(1) heating filament electrical resistance of said heating filament at a given temperature,
(2) heating filament heat transfer efficiency of said heating filament, and
(3) heating filament temperature coefficient of resistance of said heating filament;
(b) patient specific information;
(iii) an electrical connector electrically connected to said heating filament and at said proximal end of said catheter assembly for enabling said heating filament to communicate with said external processing system, wherein said predetermined location is at said connector and said connector comprises electrical leads which are electrically connected to said memory and
(B) an external processing system which is connectable to said catheter assembly so that the external processing system can communicate with said memory and said heating filament, said external processing system comprising:
(i) means for decoding said encoded heating filament calibration information stored in said memory for generating decoded heating filament calibration information and
(ii) means for calculating cardiac output using said decoded heating filament calibration information;
(iii) means for displaying said patient specific information as trending data; wherein:
(i) said connector and said memory are functionally interrelated by said electrical leads to enable access to said encoded thermodilution information stored in said memory by said external processing system and system of claim 18,
(ii) said external processing system, said connector, and said memory are functionally interrelated so that said external processing system can access said patient specific information that is stored in said memory via said electrical leads.

23. A thermodilution catheter assembly system for calculating a patient's cardiac output, comprising:
(A) a catheter assembly comprising
(i) a catheter adapted to be inserted into the patient's bloodstream, said catheter having a heating filament made of a thin, flexible material having a temperature coefficient of resistance of at least 0.001 ohms per ohm-degree centigrade; and
(ii) a memory which resides at a predetermined location on or about said catheter, said memory storing encoded thermodilution information comprising
(a) heating filament calibration information, said heating filament calibration information comprising
(2) heating filament electrical resistance of said heating filament at a given temperature,
(2) heating filament heat transfer efficiency of said heating filament, and
(3) heating filament temperature coefficient of resistance of said heating filament and
(B) an external processing system which is connectable to said catheter assembly so that the external processing system can communicate with said memory and said heating filament, said external processing system comprising
(i) means for decoding said encoded heating filament calibration information stored in said memory for generating decoded heating filament calibration information and
(ii) means for calculating cardiac output using said decoded heating filament calibration information; and wherein said memory further contains at least one of a computer program, a computer program segment, and a software subroutine which can be read by said external processing system and used thereby to verify, correct, or modify processing of said thermodilution information.

24. A thermodilution catheter assembly for use in determining a patient's cardiac output comprising:
(i) a catheter adapted to be inserted into a patient's bloodstream, said catheter having a heating filament made of a thin, flexible material having a temperature coefficient of resistance of greater than 0.001 ohms per ohm-degree centigrade; and
(ii) a memory which resides at a predetermined location on or about said catheter, said memory storing thermodilution information comprising
(a) heating filament calibration information, said heating filament calibration information comprising at least one of
(1) heating filament electrical resistance of said heating filament at a given temperature,
(2) heating filament heat transfer efficiency of said heating filament, or
(3) heating filament temperature coefficient of resistance of said heating filament, and
(b) patient specific information.

25. The thermodilution catheter assembly of claim 24, wherein said patient specific information comprises patient historical data.

26. The thermodilution catheter assembly of claim 24, wherein said thermodilution information further comprises catheter identification information.

27. A thermodilution catheter assembly for insertion in an artery or a vein for use in determining a patient's cardiac output, comprising:
(i) a catheter adapted to be inserted into a patient's bloodstream, said catheter having a heating filament made of a thin, flexible material having a temperature coefficient of resistance of at least 0.001 ohms per ohm-degree centigrade; and
(ii) a memory which resides at a predetermined location on or about said catheter, said memory storing thermodilution information comprising
(a) heating filament calibration information, said heating filament calibration information comprising at least one of
(1) heating filament electrical resistance of said heating filament at a given temperature,
(2) heating filament heat transfer efficiency of said heating filament, or
(3) heating filament temperature coefficient of resistance of said heating filament, and
(b) operation information comprising at least one of
(1) a computer program,
(2) a computer program segment, and
(3) a software subroutine.

28. The thermodilution catheter assembly of claim 27, wherein said operation information comprises information for controlling processing of said thermodilution information.

29. The thermodilution catheter assembly of claim 28, wherein said operation information comprises information for controlling processing of said thermodilution information to verify, correct, or modify said thermodilution information.

30. The thermodilution catheter assembly of claim 28, wherein said operation information comprises information for controlling processing of said thermodilution information by an external processing system to verify, correct, or modify said thermodilution information.

31. The thermodilution catheter assembly of claim 28, wherein said operation information comprises information for controlling processing of said thermodilution information for calculating the patient's cardiac output.

32. A thermodilution catheter assembly system for calculating a patient's cardiac output, comprising:
   (A) a catheter assembly comprising
      (i) a catheter adapted to be inserted into a patient's bloodstream, said catheter having a heating filament made of a thin, flexible material having a temperature coefficient of resistance of at least 0.001 ohms per ohm-degree centigrade;
      (ii) a memory which resides at a predetermined location on or about said catheter, said memory storing thermodilution information comprising
         (a) heating filament calibration information, said heating filament calibration information comprising at least one of
            (1) heating filament electrical resistance of said heating filament at a given temperature,
            (2) heating filament heat transfer efficiency of said heating filament, or
            (3) heating filament temperature coefficient of resistance of said heating filament, and
         (b) operation information comprising at least one of
            (1) a computer program,
            (2) a computer program segment, and
            (3) a software subroutine;
   (B) an external processing system adapted to communicate with said memory to read said thermodilution information and to communicate with said heating filament to determine resistance of said heating filament; and
      wherein said external processing system and said operation information, in combination, comprise means for calculating the patient's cardiac output by processing said thermodilution information.

33. The thermodilution catheter assembly system of claim 32, wherein said operation information comprises information for controlling processing of said thermodilution information.

34. The thermodilution catheter assembly system of claim 32, wherein said operation information comprises information for controlling processing of said thermodilution information to verify, correct, or modify said thermodilution information.

35. A thermodilution catheter assembly for providing data to an external processing system for calculating a patient's cardiac output, comprising:
   (i) a catheter adapted to be inserted into a patient's bloodstream, said catheter having a heating filament made of a thin, flexible material having a temperature coefficient of resistance of at least 0.001 ohms per ohm-degree centigrade;
   (ii) means, mounted to said catheter, for measuring data relating to cardiac output; and
   (iii) a memory which resides at a predetermined location on or about said catheter, said memory storing operation information for controlling calculation of the patient's cardiac output based upon data including said data relating to cardiac output that is measured by said means for measuring, said operation information comprising at least one of
      (1) a computer program,
      (2) a computer program segment, and
      (3) a software subroutine.

36. The thermodilution catheter assembly of claim 35, wherein said operation information comprises information for controlling calculation of the patient's cardiac output by an external processing system.

37. A thermodilution catheter assembly for use in determining a patient's cardiac output, comprising:
   a catheter adapted to be inserted into a patient's bloodstream, said catheter having a heating filament made of a thin, flexible material having a temperature coefficient of resistance of at least 0.001 ohms per ohm-degree centigrade; and
   a memory which resides at a predetermined location on or about said catheter, said memory storing thermodilution information comprising patient specific information.

38. A thermodilution catheter assembly of claim 37, wherein said patient specific information comprises patient historical data.

39. A thermodilution catheter assembly for use in determining a cardiac output of a patient, comprising:
   a catheter adapted to be inserted into a bloodstream of the patient, said catheter having a heating filament made of a thin, flexible material having a temperature coefficient of resistance of greater than zero; and
   a memory which resides at a predetermined location on or about said catheter, said memory storing thermodilution information comprising heating filament calibration information.

40. The thermodilution catheter assembly of claim 39, wherein said heating filament calibration information comprises heating filament electrical resistance of said heating filament at a given temperature.

41. The thermodilution catheter assembly of claim 40, wherein said temperature coefficient of resistance is at least 0.001 ohms per ohm-degree centigrade.

42. The thermodilution catheter assembly of claim 39, wherein said heating filament calibration information comprises heating filament heat transfer efficiency of said heating filament.

43. The thermodilution catheter assembly of claim 41, wherein said temperature coefficient of resistance is at least 0.001 ohms per ohm-degree centigrade.

44. The thermodilution catheter assembly of claim 39, wherein said heating filament calibration information comprises heating filament temperature coefficient of resistance of said heating filament.

45. The thermodilution catheter assembly of claim 42, wherein said temperature coefficient of resistance is at least 0.001 ohms per ohm-degree centigrade.

46. A thermodilution catheter assembly for providing data to an external processing system for calculating a cardiac output of a patient, comprising:
   a catheter adapted to be inserted into a bloodstream of the patient, said catheter having a heating filament made of a thin, flexible material having a temperature coefficient of resistance of greater than zero;
   means, mounted to said catheter, for measuring data relating to cardiac output; and a memory which resides at a predetermined location on or about said catheter, said memory storing operation information for controlling calculation of the patient's cardiac output based upon data including said data relating to cardiac output that is measured by said means for measuring.

47. The thermodilution catheter assembly of claim 46, wherein said operation information comprises a computer program.

48. The thermodilution catheter assembly of claim 47, wherein said temperature coefficient of resistance is at least 0.001 ohms per ohm-degree centigrade.

49. The thermodilution catheter assembly of claim 46, wherein said operation information comprises a computer program segment.

50. The thermodilution catheter assembly of claim 48, wherein said temperature coefficient of resistance is at least 0.001 ohms per ohm-degree centigrade.

51. The thermodilution catheter assembly of claim 46, wherein said operation information comprises a software subroutine.

52. The thermodilution catheter assembly of claim 49, wherein said temperature coefficient of resistance is at least 0.001 ohms per ohm-degree centigrade.

53. The thermodilution catheter assembly of claim 46, wherein said operation information comprises information for controlling calculation of the patient's cardiac output by an external processing system.

54. The thermodilution catheter assembly of claim 50, wherein said temperature coefficient of resistance is at least 0.001 ohms per ohm-degree centigrade.

55. A thermodilution catheter system for use in determining cardiac output of a patient, comprising:
   (i) a catheter adapted to be inserted into a bloodstream of the patient, said catheter comprising
      (A) a heating filament
         (1) made of a thin and flexible material,
         (2) having a resistance, and
         (3) having a temperature coefficient of resistance of greater than zero and
      (B) a memory, said memory storing thermodilution information comprising heating filament calibration information for said heating filament; and
   (ii) means, coupled to said memory and said heating filament, for controlling the temperature of said heating filament based at least in part upon said heating filament calibration information stored in said memory.

56. The thermodilution catheter system of claim 55, wherein said heating filament calibration information stored in said memory comprises the heating filament electrical resistance of said heating filament at a given temperature.

57. The thermodilution catheter system of claim 56, wherein said temperature coefficient of resistance is at least 0.001 ohms per ohm-degree centigrade.

58. The thermodilution catheter system of claim 55, wherein said heating filament calibration information stored in said memory comprises the heating filament heat transfer efficiency of said heating filament.

59. The thermodilution catheter system of claim 57, wherein said temperature coefficient of resistance is at least 0.001 ohms per ohm-degree centigrade.

60. The thermodilution catheter system of claim 55, wherein said heating filament calibration information stored in said memory comprises the heating filament temperature coefficient of resistance of said heating filament.

61. The thermodilution catheter system of claim 58, wherein said temperature coefficient of resistance is at least 0.001 ohms per ohm-degree centigrade.

62. The thermodilution catheter system of claim 55, wherein said thermodilution information further comprises patient specific information.

63. The thermodilution catheter system of claim 55, wherein said memory further stores at least one of a computer program, a computer program segment, and a software subroutine.

64. The thermodilution catheter system of claim 63, wherein said at least one of a computer program, a computer program segment, and a software subroutine can be used to verify, correct, or modify processing of said thermodilution information.

* * * * *